(12) United States Patent
Schafer et al.

(10) Patent No.: US 7,223,855 B2
(45) Date of Patent: May 29, 2007

(54) HYDROPEROXIDE LYASE REGULATOR REGION

(75) Inventors: Ulrike Schafer, Saskatoon (CA); Dwayne Hegedus, Saskatoon (CA); Nicholas J. Bate, Urbandale, IA (US); Stephen Gleddie, Ottawa (CA); Daniel C. W. Brown, Ilderton (CA)

(73) Assignee: Her Majesty the Queen in right of Canada, as represented by the Minister of Agriculture and Agri-Food, Saskatoon, SK (CA)

( * ) Notice: Subject to any disclaimer, the term of this patent is extended or adjusted under 35 U.S.C. 154(b) by 378 days.

(21) Appl. No.: 10/204,234

(22) PCT Filed: Dec. 17, 2001

(86) PCT No.: PCT/CA01/01802

§ 371 (c)(1),
(2), (4) Date: Dec. 30, 2002

(87) PCT Pub. No.: WO02/50291

PCT Pub. Date: Jun. 27, 2002

(65) Prior Publication Data

US 2003/0163835 A1    Aug. 28, 2003

Related U.S. Application Data

(60) Provisional application No. 60/256,625, filed on Dec. 18, 2000.

(51) Int. Cl.
*A01H 1/00* (2006.01)
*C07H 21/04* (2006.01)
*C12N 15/09* (2006.01)

(52) U.S. Cl. ............... 536/24.1; 435/6; 435/69.1; 435/71.1; 435/419; 435/320.1; 536/23.1; 800/278; 800/295

(58) Field of Classification Search ............ 800/295; 435/320.1; 536/23.1
See application file for complete search history.

(56) References Cited

U.S. PATENT DOCUMENTS 5,824,872 A    10/1998   Miki et al.
6,118,049 A *   9/2000   Bestwick et al. ............ 800/283

FOREIGN PATENT DOCUMENTS

| EP | 0801133 A2 | 10/1997 |
|---|---|---|
| WO | WO 99/07857 | 2/1999 |
| WO | WO 00/00627 | 1/2000 |
| WO | WO 00/22145 | 4/2000 |
| WO | WO 00/50575 | 8/2000 |

OTHER PUBLICATIONS

Bevan et al. Accession No. Z97338. Date: Aug. 1999, Database: GenBank.*
Kim et al. Plant Mol Biol. 1994. vol. 24, pp. 105-117.*
Bate NJ, Sivasankar S, Moxon C, Riley JMC, Thompson JE, Rothstein SJ, Molecular Characterization of an Arabidopsis Gene Encoding Hydroperoxide Lyase, a Cytochrome P-450 That Is Wound Inducible, Plant Physiol. (1998) 117:1393-1400.
Matsui K, Shibutani M, Hase T, Kajiwara T. Bell pepper fruit fatty acid hydroperoxide lyase is a cytochrome P450 (CYP74B), FEBS Lett. (1996) 394(1):21-4.
Vaughn SF, Gardner HW. Lipoxygenase-Derived Aldehydes Inhibit Fungi Pathogenic On Soybean, Journal of Chemical Ecology (1993) 19:2337-2345.

* cited by examiner

Primary Examiner—Phuong T. Bui
(74) Attorney, Agent, or Firm—Quarles & Brady LLP

(57) ABSTRACT

The invention provides for a chimeric construct comprising a regulatory region obtained from a hydroperoxide lyase (HPL) gene in operative association with a heterologous gene of interest. Even though the HPL gene is known to be expressed in response to wounding, unexpectedly, it was observed that the HPL regulatory region or one or more fragments thereof, result in constitutive expression of the gene of interest in a range of tissues and organs in the absence of any wound or stress treatment. This invention also provides for a transgenic organism comprising the chimeric construct defined above, and a method for preparing a transgenic organism using the chimeric construct.

16 Claims, 6 Drawing Sheets

FIGURE 1A

```
-1419 GCCATAACGT GGATACTTGG CAGTGGTTAC TTGGCTTTC  CTTTATTTC  TTTTGGACGG AAGCGGTGGT TACTTTGTCA
-1339 CACATTTAAA AAACACGTG  TTTCTCACTC TTTTCTATTC CCGTCACAAA CAATTGTAAG AAAGATGAAT CTATCGTGAT
       ******
-1259 CTTTCTATCA AACAAAAGAA AAAAGTCTT  CATAGTAACG CTACAACATC AAATATGTGG TTGCTCTGAC ATCAGTCGGG
-1179 AAATAAGGA  TATGCGGCCA TTGGCCACAT CTATGGGGT   CCCAACTTCC TTTCACAAAA AAATAAATT  GGGTGACCCA
-1099 ACTTTATCT  TTGATATAGT GACATGAGTA TCGGAGCAT  TGGACAATGG ATAAAATGAG AACTAAACAA AATCTGGTTA
-1019 ATTTTGATC  ATTGTTATTT AAAGGTTAT  TTTATCTATA ATCTACCCAT ATTGATCAGT TTTATTTAAA TTTGTTTAGC
-939 TACCGCTCCT CGAGAGAGAT GTCCATGGAC ATTCTTTGGA AAAATGGAAT CACACGACCC CAAAAGTATA TTTTTCTCT
     ***        +++++     +
-859 GGAGAATGCT ATTTAGAGCT TTGACTATAT GGTCTGAATT AGAAAGACGG GAAATAAAAT CTGCTAAGTG ATATAAGCTC
-779 TAAGTAGGCG ATGTGTGATG GAGAGACACCT TTTCTTCATG AGTCTTCATG TTTTACAGAT TCGCGAACTT CGAATATCCC
-699 TATACGGTCT GTCAACCCT  CGTGTGTCTT TTGAGTCCAA GATAAGGGCC ATTATTGAGT AACATAGACA TGCTGGAATC
                                                                                   ****
-619 CAACCATTGA AGTCACAACT GTCCATGAAC ATTCTTTGGA GAATCTGAAA AGTCTTATA  AAGGTGGTGT TTCAAAGAAA
     ***       +++++    +
-539 ACAAACAAT  TGAGTTAAGA AAAAAAATA  TCATGTAGTG GTCGAGTATT ATGTTATTTA TGTGTAGCT  ACCAATCTTT
     +++++     ++
-459 ATTCTTTAAA TCTGACATAA AATGCTAACA ACTTTTTACC TCGTCTATAG CCCCAAAAAA CCTAACCACG GTTCTAAAAC
                                                                     *    ****
-379 CACACACAGT GATTTTGGTT GACGACAATG CCCTCTCCTTC CTCAAAACGA TTTATTTACA TTTTTAAAT  CAAATGTTAC
                         ****                                                    ++++++
-299 ATTTTATACC ATAATTAAGT CTTTTTACAG AATACTTAGA TGGAAGAGAT GTATAAAAAA GGAGGAAATT GTAAAAAACA
-219 TATTTCGATC AATTAAACCA GGATTCATAA AAATAAGT    ATGATGTTC  GTTTAGCGAT GAACTTCACT
-139 CCAATGATAA TACTTAACAA TATAAGTACA TAAAAATAA  TAAAAATAA  AATTGTTACG AAAAGTCTAC AAATACTGCA
     ++++++                                                           +1         =
-59  TGGATAAGTA ATGTCTCTT  TATTTATTTA TTATACCTT  ACCAAGATAT ATCTATAACC GCATAGAAT  AGAAGGCGAA
+21  GAGATAATT  CCAAAAACAA GAAAAACCTC TAAGCTCAAA AGATGTGTT  GAGAACGATG CGGGCGACTT CCCCGGGCCC
             M  L  L  R  T  M     A  A  T     S  P  R  P
```

HYDROPEROXIDE LYASE REGULATOR REGION

CROSS-REFERENCE TO RELATED APPLICATIONS

This application is the national stage application of PCT Application No. PCT/CA01/01802 filed Dec. 17, 2001 which claimed priority to U.S. Provisional Application No. 60/256,625 filed Dec. 18, 2000.

The present invention relates to the regulation of gene expression. More specifically, this invention pertains to the characterization of the Hydroperoxide Lyase (HPL) regulatory region, and the use of one or more HPL regulatory regions to drive gene expression.

BACKGROUND OF THE INVENTION

Hydroperoxide Lyase (HPL) catalyzes the cleavage of hydroperoxide lipids to form six carbon volatile compounds and a 12-Carbon product. The C6-volatiles are responsible for the "green-note" flavour characteristic of plant products and have been discussed as playing a role in the defence response in plants. For example, the volatile aldehydes are known to exhibit anti-fungal (Vaughn et al 1993, J. Chem Ecol. 19:2337–2345), anti-bacterial and anti-insect (Matsui et al 1986, FEBS Let. 394:21–24) activities. The C12 compound gives rise to thaumatin a wound-related signalling compound. The cleavage of hydroperoxide lipids also produces jasmonic acid that is also involved in stress and disease resistance signalling. WO 00/00627 and Matsui (1986 FEBS Let. 394:21–24) describe increased expression of HPL in wounded plants.

The HPL gene has been cloned from bell pepper (WO 00/00627; Matsui et al. 1986, FEBS Let. 394:21–24), maize (WO 00/22145), banana (EP 0 801 133) and *Arabidopsis* (Bate et al., 1998. Plant Physiol. 117:1393–1400; WO 00/00627), and the preparation of expression cassettes to increase or decrease HPL expression within these plants is described. The HPL gene has been sequenced by the *Arabidopsis* genome sequencing project (Accession number: Z97339) and reveals an open reading frame interrupted by eight introns. However, there is no teaching of the characterization of the regulatory region of HPL.

As described herein, the upstream region of the HPL gene has been characterized and used to drive the expression of a gene of interest. Even though the HPL regulatory region is known to drive wound-, insect-, fungal-, and bacterial-induced expression, unexpectedly, it was observed that large portions of the HPL regulatory region and fragments thereof, resulted in constitutive expression of the gene of interest in a range of tissues and organs in the absence of any wound or stress treatment. Therefore, the present invention relates to providing a regulatory region capable of driving expression of a gene of interest.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to the regulation of gene expression. More specifically, this invention pertains to the characterization of the Hydroperoxide Lyase (HPL) regulatory region, and the use of one or more HPL regulatory regions to drive gene expression.

According to the present invention there is provided a chimeric construct comprising a regulatory region obtained from an HPL gene in operative association with a heterologous gene of interest.

This invention pertains to the chimeric construct as defined above wherein the regulatory region comprises a nucleic acid sequence of SEQ ID NO:1, a fragment thereof, or a nucleotide sequence that hybridizes to SEQ ID NO:1 under the following conditions: 0.5 M $NaHPO_4$ pH7.2, 7% SDS, 1% BSA, 1 mM EDTA, at 65° C., followed by washing in 40 mM $NaHPO_4$ pH7.2, 5% SDS, at 65° C., and washing in 40 mM $NaHPO_4$ pH7.2, 1% SDS, 1 mM EDTA, at 65° C. Preferably, the chimeric construct of the present invention is defined by the nucleic acid sequence of SEQ ID NO:1.

The present invention also provides for a transgenic organism comprising the chimeric construct as defined above. The transgenic organism is selected from the group consisting of a plant, insect, fungi, animal, and prokaryote. Preferably, the transgenic organism is a plant. This invention also includes a transgenic cell culture comprising the chimeric construct as defined above.

This invention also provides for transgenic seed, comprising the chimeric construct as defined above.

The present invention also pertains to a method of regulating the expression of a gene of interest in an organism comprising;
  i) transforming the organism with the chimeric construct as defined above to produce a transformed organism; and
  ii) growing the transformed organism.

This method, after the step of transforming, may include a step of determining the expression of the gene of interest within the transformed organism. Furthermore, after the step of growing, progeny comprising the gene of interest may be obtained.

This invention includes the method as defined above where the organism is a plant.

The present invention also embraces a chimeric construct as defined above wherein the regulatory region is in operative association with a second heterologous regulatory region, so that both the regulatory region and the second regulatory region operate together to regulate the expression of a gene of interest.

The present invention also provides a second method of regulating the expression of a gene of interest in an organism comprising;
  i) transforming said organism with a chimeric construct, to produce a transformed organism, the chimeric construct comprising a regulatory region in operative association with a second heterologous regulatory region, so that, both the regulatory region and the second regulatory region operate together to regulate the expression of a gene of interest; and
  ii) growing the transformed organism.

As described herein, the present invention provides for a regulatory region, or a fragment thereof, obtained from an HPL gene. This regulatory region may be used to drive the expression of a gene of interest within any desired organism. Even though the HPL gene is known to be expressed in response within plants to wounding, insect, fungal, or bacterial-induced wounding, unexpectedly, the HPL regulatory region and fragments thereof, result in constitutive expression of a gene of interest in a range of tissues and organs in a plant, in the absence of any wound or stress treatment. Therefore, it is to be understood that the regulatory region as described herein maybe used to drive or mediate the expression of any gene of interest in any organism.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 1 shows the structure of the *Arabidopsis* hydroperoxide lyase gene. FIG. 1A) shows the sequence of the regions upstream of the HPL open reading frame used to direct reporter gene expression. The transcription start site is labelled as +1. The putative TATA and CAAT boxes are double underlined. Single underlining denotes the DNA regions used to PCR amplify the upstream region. The G-box, rbcS consensus site, MYB consensus site and the ASF-1 binding site are underlined with asterisks. The E-boxes are underlined with plus signs.

FIG. 2(A) shows GUS activity in root tissue. FIG. 2(B) shows flower tissue stained for GUS, showing strong expression in the sepals, with reduced expression in the pollen sacs, petals and the stigma. FIG. 2(C) shows GUS activity staining in seedling leaf tissue and root tips.

DESCRIPTION OF PREFERRED EMBODIMENT

Figure 2:
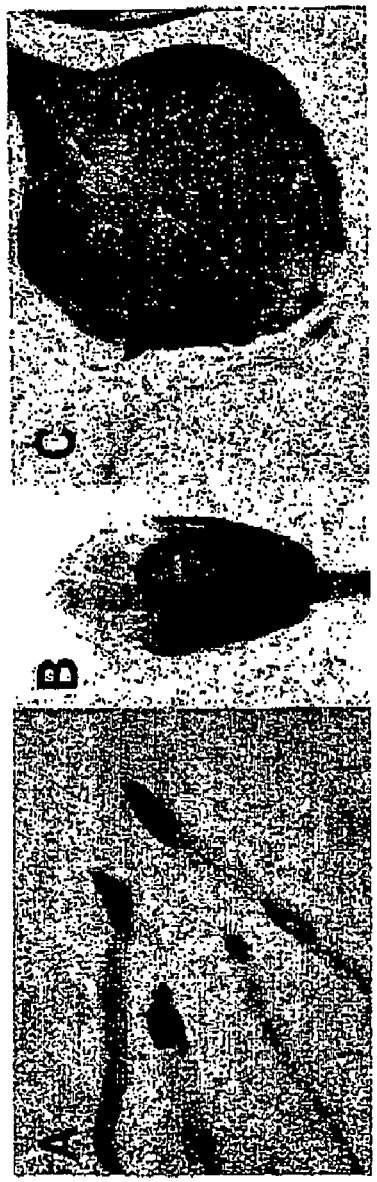
FIG. 2 shows HPL-driven gene expression as demonstrated using histochemical staining for GUS activity.

The present invention relates to the regulation of gene expression. More specifically, this invention pertains to the characterization of the Hydroperoxide Lyase (HPL) regulatory region, and the use of one or more HPL regulatory regions to drive gene expression.

The following description is of a preferred embodiment by way of example only and without limitation to the combination of features necessary for carrying the invention into effect.

The present invention relates to the characterization of the regulatory region and fragments thereof, from HPL. The regulatory region and fragments thereof may be used to drive the expression of a gene of interest within any tissue, or organ of interest, for example, but not limited to tissues and organs within a plant. It is to be understood that the present invention is not limited to any plant. Rather, the regulatory region as described herein, and fragments thereof, may be used to drive the expression of a gene of interest within, for example, but not limited to monocots and dicots including agricultural and horticulturally important species, trees, gymnosperms and the like. It is also contemplated that the HPL regulatory region or a fragment thereof may be used to mediate expression of a gene of interest within a cell culture, or any desired organism, including for example, but not limited to, prokaryotes, fungi, insects, and animals.

By "gene of interest" it is meant any gene that is to be expressed in a transformed organsim, for example, but not limited to a plant. Any exogenous gene can be used and manipulated according to the present invention to result in the expression of said exogenous gene. A DNA or gene of interest may include, but is not limited to, a gene encoding a protein, a DNA that is transcribed to produce antisense RNA, or a transcript product that functions in some manner that mediates the expression of other DNAs, for example that results in the co-suppression of other DNAs or the like. Such a gene of interest may also include, but is not limited to, a gene that encodes a pharmaceutically active protein, for example growth factors, growth regulators, antibodies, antigens, their derivatives useful for immunization or vaccination and the like. Such proteins include, but are not limited to, interleukins, insulin, G-CSF, GM-CSF, hPG-CSF, M-CSF or combinations thereof, interferons, for example, interferon-α, interferon-β, interferon-τ, blood clotting factors, for example, Factor VIII, Factor IX, or tPA or combinations thereof. A gene of interest may also encode an industrial enzyme, protein supplement, nutraceutical, or a value-added product for feed, food, or both feed and food use. Examples of such proteins include, but are not limited to proteases, oxidases, phytases, chitinases, invertases, lipases, cellulases, xylanases, enzymes involved in oil biosynthesis etc. Other protein supplements, nutraceuticals, or a value-added products include native or modified seed storage proteins and the like. Furthermore, a gene of interest may encode one or more proteins that confer herbicide or pesticide resistance to an organism, or encode a protein that is involved in the regulation of gene expression of other genes or transgenes.

The present invention provides and characterizes the regulatory region disclosed in SEQ ID NO:1, and fragments thereof. Preferably, the regulatory region comprises the sequence of nucleotide 1–1480 of SEQ ID NO:1. Chimeric constructs, comprising the regulatory region or a fragment thereof, in operative association with a gene of interest maybe used to drive the expression of the gene of interest within an organism of choice. Furthermore, the present invention pertains to genetic constructs that comprise portions of the HPL regulatory region in operative association with one or more heterologous regulatory regions, for example but not limited to, enhancer or silencer regions, or constitutive, inducible, tissue dependant, temporally dependant regulatory regions, or a post-transcriptional or translational enhancer regulatory element, in operative association with a gene of interest.

The chimeric gene construct of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. Examples of suitable 3' regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes and the small subunit of the ribulose-1, 5-bisphosphate carboxylase (ssRUBISCO) gene. The 3' untranslated region from the structural gene of the present construct can therefore be used to construct chimeric genes for expression in plants.

The chimeric gene construct of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA.

To aid in identification of transformed plant cells, the constructs of this invention may be further manipulated to include plant selectable markers. Useful selectable markers include enzymes which provide for resistance to an antibiotic such as gentamycin, hygromycin, kanamycin, and the like. Similarly, enzymes providing for production of a compound identifiable by colour change such as GUS (β-glucuronidase), or luminescence, such as luciferase are useful.

Also considered part of this invention are transgenic plants containing the chimeric gene construct comprising a chimeric gene as described herein. However, it is to be understood that the gene of the present invention may also be combined with a range of regulatory elements for expression within a range of host organisms. Such organisms include, but are not limited to angiosperms, monocots or dicots, for example, corn, wheat, barley, oat, tobacco, Brassica, soybean, bean, pea, alfalfa, potato, *Arabidopsis*, tomato, peach, grape, sunflower, cauliflower, cotton, spruce.

Methods of regenerating whole plants from plant cells are also known in the art. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

By "transformation" it is meant the stable interspecific transfer of genetic information that is manifested phenotypically. The constructs of the present invention can be introduced into plant cells using Ti plasmids, Ri plasmids, plant virus vectors, direct DNA transformation, micro-injection, electroporation, etc as would be known to those of skill in the art. For reviews of such techniques see for example Weissbach and Weissbach, *Methods for Plant Molecular Biology*, Academy Press, New York VIII, pp. 421–463 (1988); Geierson and Corey, *Plant Molecular Biology*, 2d Ed. (1988); and Miki and Iyer, *Fundamentals of Gene Transfer in Plants*. In *Plant Metabolism*, 2d Ed. D T. Dennis, D H Turpin, D D Lefebrve, D B Layzell (eds), Addison Wesly, Langmans Ltd. London, pp. 561–579 (1997). The present invention fisher includes a suitable vector comprising the chimeric gene construct.

The DNA sequences of the present invention thus include the DNA sequences of SEQ ID NO: 1, and fragments or derivatives thereof, as well as analogues of, or nucleic acid sequences comprising about 80% similarity with the nucleic acids as defined in SEQ ID NO: 1 as determined using hybridization or nucleotide alignment algorithins. Analogues include those DNA sequences which hybridize under stringent hybridization conditions, for example but not limited to hybridizing overnight in 0.5 M $NaHPO_4$ pH 7.2, 7% SDS, 1% BSA, 1 mM EDTA, at 65° C., followed by washing 2 times in 40 mM $NaHPO_4$ pH7.2, 1 mM EDTA, 5% SDS for 5 min each, and a further 4 washes, for 5 min each, in 40 mM $NaHPO_4$ pH7.2, 1 mM EDTA, 1% SDS, at 65° C., (see Maniatis et al., in Molecular Cloning (A Laboratory Manual), Cold Spring Harbor Laboratory, 1982, p. 387–389) to the DNA sequence of SEQ ID NO: 1, provided that said sequences maintain at least one property of the activity of the gene as defined herein. Homology determinations may also be made using oligonucleotide alignment algorithms for example, but not limited to a BLAST (GenBank see ncbi.nlm.nih.gov/cgi-bin/BLAST/, using default parameters: Program: blastn; Database: nr; Expect 10; filter: efault; Alignment: pairwise; Query genetic Codes: Standard(1)) or FASTA, again using default parameters.

By "DNA regulatory region" it is meant a nucleic acid sequence that has the property of controlling the expression of a DNA sequence that is operably linked with the regulatory region. Such regulatory regions may include promoter or enhancer regions, and other regulatory elements recognized by one of skill in the art. By "promoter" it is meant the nucleotide sequences at the 5' end of a coding region, or fragment thereof that contain all the signals essential for the initiation of transcription and for the regulation of the rate of transcription. The promoters used to exemplify the present invention are constitutive promoters that are known to those of skill in the art. However, if tissue specific expression of the gene is desired, for example seed, or leaf specific expression, then promoters specific to these tissues may also be employed. Furthermore, as would be known to those of skill in the art, in ducible promoters may also be used in order to regulate the expression of the gene following the induction of expression by providing the appropriate stimulus for inducing expression. In the absence of an inducer the DNA sequences or genes will not be transcribed. Typically the protein factor, that binds specifically to an inducible promoter to activate transcription, is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible promoter may be exposed to an inducer by externally applying the inducer to the cell or plant such as by spraying, watering, heating or similar methods.

A constitutive regulatory element directs the expression of a gene throughout the various, but not necessarily all, parts of a plant and continuously throughout plant development. Examples of known constitutive regulatory elements include promoters associated with the CaMV 35S transcript. (Odell et al., 1985, *Nature,* 313:810–812), the rice actin 1 (Zhang et al, 1991, *Plant Cell,* 3: 1155–1165) and triosephosphate isomerase 1 (Xu et al, 1994, *Plant Physiol.* 106: 459–467) genes, the maize ubiquitin 1 gene (Cornejo et al, 1993, *Plant Mol. Biol.* 29: 637–646), the *Arabidopsis ubiquitin* 1 and 6 genes (Holtorf et al, 1995, *Plant Mol. Biol.* 29:637–646), T1275 (also known as TCUP; U.S. Pat. No. 5,824,872) and the tobacco translational initiation factor 4A gene (Mandel et al, 1995 *Plant Mol. Biol.* 29: 995–1004).

Also considered part of this invention are transgenic organisms, for example but not limited to prokaryotes, fungi, plants, insects, or animals containing the gene construct of the present invention. In the case of the transgenic organism being a plant, methods of regenerating whole plants from plant cells are known to those of skill in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

Figure 1B:
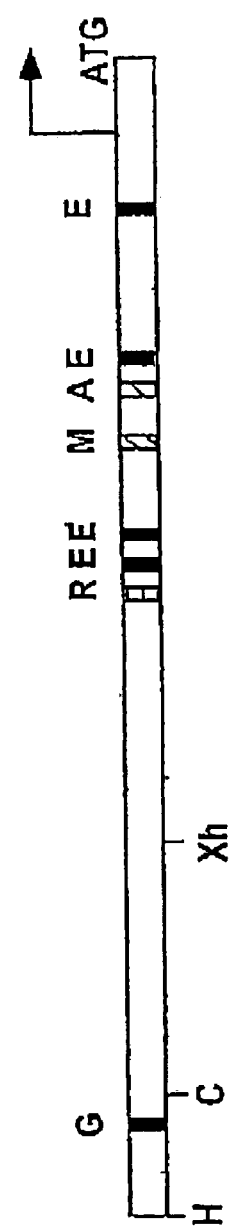
FIG. 1B) shows the schematic of the upstream region showing the location of putative cis-regulatory sequences and restriction enzyme sites. Letters above the sequence denote the type of consensus site (G, G-box; R, rbcS; E, E-box; M, MYB; A, ASF1 motif). Restriction enzyme sites are: C, ClaI; Xh, XhoI.

The transcriptional start of the HPL gene is known to occur at the cytosine nucleotide (−78 from the translational start; Bate et al 1998). Sequence comparison of the HPL upstream sequence using the PLACE database see-dna.af-frc.go.jp/htdocs/PLACE/), to known cis-regulatory regions of previously characterized plant promoters, indicates that 23 nucleotides upstream from the transcriptional start is a TATA sequence (position 1388–1391 of SEQ ID NO:1), and approximately 40 nucleotides further upstream is a putative CAAT box (actual sequence CAAAT; position 1345–1350 of SEQ ID NO:1). Both sequences are double-underlined in FIG. 1A. Detailed analysis of the sequence revealed numerous GATA box sequences and other putative regulatory elements. Most noticeably, a G-box (CACGTG) is present at −1320 (nucelotides 90–95 of SEQ ID NO:1), as well as several E-boxes (CANNTG; nucleotides 811–816; 882–887; 1106–1111; 1276–1282 of SEQ ID NO:1). In addition, two cis-regulatory regions correlated with strong transcriptional regulation are present: the ASF1 motif (cauliflower mosiac virus 35S promoter) is present at −359 (nucelotides 1055–1059 of SEQ ID NO:1) and an rbcS consensus is present at −623 (nucleoitdes 792–798 of SEQ ID NO:1). These two putative regulatory sequences are surrounded by three E-boxes (811–816; 882–887 and 1106–1111 of SEQ ID NO:1), as well as a consensus site for MYB transcription factor binding (FIGS. 1A, 1B; 1015–1021 of SEQ ID NO:1).

Characterization of HPL expression in *Arabidopsis* indicates that the HPL mRNA accumulates to low levels in mature leaf tissue, but is wound-inducible. To further characterize the expression of the HPL gene in plants, the region upstream of the HPL gene was cloned using PCR and primers designed based on sequence information from the public *Arabidopsis* sequencing project. In stably transformed plants the upstream regulatory region of the HPL directed strong expression of the GUS reporter gene in vegetative tissues including roots.

All of the transformants showed strong GUS staining throughout leaf tissue, both in young seedlings and mature plants. FIG. 2 demonstrates that the HPL regulatory region is active and drives the expression of a gene of interest in the root tips of young roots (FIG. 2A), the floral sepals (FIG. 2B) as well as the entire leaf (FIG. 2C). However, activity of the HPL regulatory was not observed in the petals, style or pollen (FIG. 2B). Such an expression pattern may prove beneficial in circumstances where expression of a gene of interest is not desired in the floral tissues, for example to minimize the effects of a recombinant insecticidal protein on a non-target insect targets, for example butterflies feeding on pollen.

The activity of the HPL regulatory region within roots, sepals and leaves, in the absence of wounding, is in contrast with the pattern of expression for the endogenous HPL gene as demonstrated by Northern blot analysis and RT-PCR, where only low levels of expression were present in leaf tissue. Without wishing to be bound by theory, it is possible that there are post-transcriptional mechanisms govern the level of HPL mRNA accumulation in leaves or alternatively, that the approximately 1.5 kb fragment characterized here is missing a repressor element further upstream. The absence of a repressor element would therefore allow strong expression from the HPL regulatory region or a fragment thereof, in transgenic plants.

The expression pattern of the HPL regulatory region distinguishes it from those that drive photosynthesis-related gene expression, such as rbcS or LHCP. In photosynthesis-associated promoters, expression is absent from root tissue and is dependent upon a photosynthetic chloroplast. HPL directed expression is clearly evident in roots, particularly in young root tips. HPL activity is also tissue-dependent, since there is no HPL-driven GUS activity in the petals, pollen sacs or stigma. It is known that HPL enzyme activity is associated with the chloroplast envelope and the N-terminus of the deduced amino acid sequence possesses structural features of a chloroplast transit peptide (Bate et al 1998). The expression pattern of the HPL mRNA, as detected by RT-PCR, demonstrates a higher level of mRNA accumulation in root and floral tissue than present in leaves. This suggests that HPL expression and activity do not require a photosynthetic chloroplast.

Furthermore, the HPL regulatory region was observed to be active in a range of organisms including but not limited to angiosperms and dicots, for example, spruce, cauliflower, soybean, alfalfa, peach, tobacco, and wheat (see Example 1). The activity of the HPL regulatory region within these plants was similar to that observed with 35S (see Table 3, Example 1).

Figure 3:
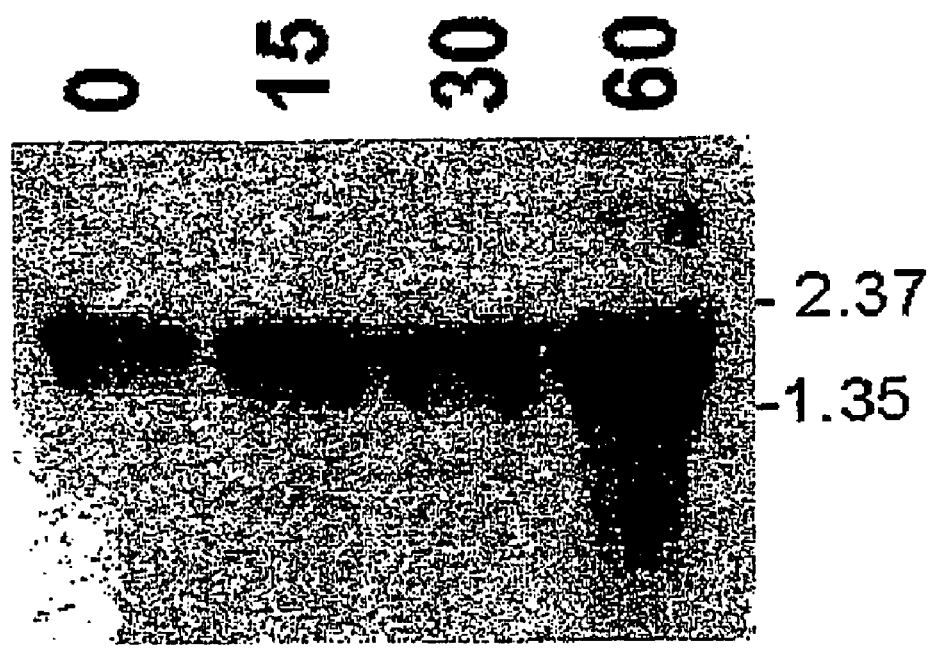
FIG. 3 shows Northern analysis of expression of HPL promoter directed GUS reporter expression before and after wounding.

In its native context within the plant genome, HPL mRNA levels increase rapidly upon wounding and are induced by methyl jasmonate (MeJA; Bate et al., 1998). To determine the inducibility of HPL-directed reporter gene expression, transformants were subjected to mechanical wounding by crushing leaf tissues with a serrated forceps as previously described (Bate et al., 1998), as well as slashing leaves with a razor blade. At various times post-injury leaves were removed from the plant and tested for GUS activity. In addition, leaves were removed and immediately frozen in liquid nitrogen. Subsequently, these RNA was isolated from these tissues and used to perform Northern blot analysis for GUS gene expression (FIG. 3). This experiment was conducted since the act of removing the leaf to test for enzyme activity constitutes an injury. Both experiments clearly demonstrated that expression of the reporter was constitutive with no significant alterations in GUS expression observed in response to wounding.

The regulatory region obtained from HPL was also used to drive the constitutive expression of PAT (phosphoinotricin-N-acetyltransferase) in plants (see Example 2), for example, in *Arabidopsis*. Plants expressing PAT under the control of the HPL regulatory region were resistant to repeated spraying with phosphinotricin.

Figure 5:
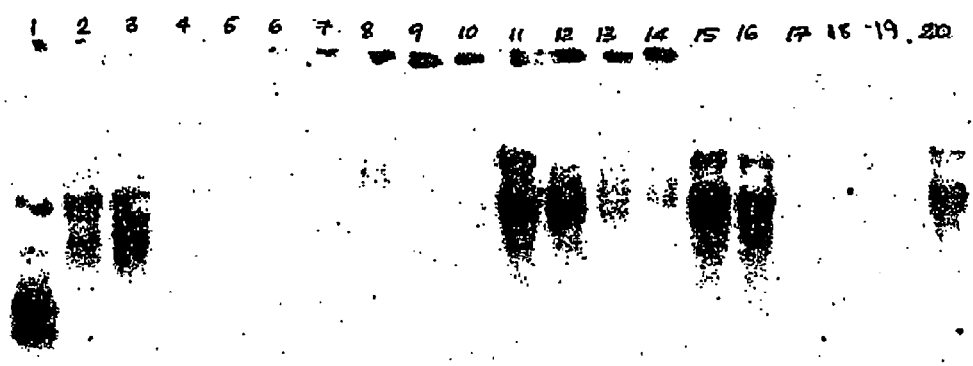
FIG. 5 shows constitutive expression of onchocystatin cysteine protease inhibitor directed by HPL promoter in *Brassica napus* cv. Westar. 15 ug of total RNA extracted from young leaves was loaded per lane, OV7 gene fragment probe was radiolabelled and the washed blot was exposed for 4 days. Lane 1-RNA ladder, Lane 2-tobacco plant expressing 70S promoter-OV7 gene, Lane 3-B. carinata plant expressing 70S promoter-OV7 gene, Lane 4-B.napus Westar non-transformed plant, Lane5-blank lane, no RNA sample, Lane 6-HPL-OV7 plant 11A, Lane 7-HPL-OV7 plant 15A, Lane 8-HPL-OV7 plant 18A, Lane 9-HPL-OV7 plant 27A, Lane 10-HPL-OV7 plant 28A, Lane 11-HPL-OV7 plant 32A, Lane 12-HPL-OV7 plant 33A, Lane 13-HPL-OV7 plant 36A, Lane 14-HPL-OV7 plant 39A, Lane 15-HPL-OV7 plant 49A, Lane 16-HPL-OV7 plant 51A, Lane 17-HPL-OV7 plant 65A, Lane 18-HPL-OV7 plant 80A, Lane 19-HPL-OV7 plant 81A, Lane 20-HPL-OV7 plant 82A.

The expression of another gene of interest, the OV7 gene encoding onchocystatin, a cysteine protease inhibitor, under the control of the HPL regulatory region was also examined in *Brassica napus* (see Example 3). As indicated in FIG. 5, OV7 transcripts under the control of the HPL regulatory region, are expressed in leaves of *B. napus* in a similar manner to that of the prior art constitutive 70S promoter.

High levels of oxalate oxidase expression under the control of the HPL regulatory region was also observed (see Table 5, Example 1). The level of HPL activity exceeded that observed with 35S.

Therefore this invention is directed to the expression of a gene of interest within any plant comprising the HPL regulatory region as defined herein, in operative association with the gene of interest.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

EXAMPLES

Example 1

HPL-GUS Expression

Expression in *Arabidopsis*

The nucleotide sequence of the HPL gene from *Arabidopsis* is known (*Arabidopsis* genome sequencing project; Accession number: Z97339) and reveals an open reading frame interrupted by eight introns. Primers were designed to amplify a 1500 bp of sequence upstream from the ATG start codon (SEQ ID NO:1; FIG. 1), the fragment was cloned into pGEM-T Easy (Promega Biotech) and sequenced. The upstream primer (5'-GGAAGCTTGCCATAACGTGG-A-3'; SEQ ID NO:2) incorporated a HindIII site, and the downstream primer (5'-TCGGATCCCATCTTTTGAGCT-3'; SEQ ID NO:3) incorporated a BamHI site to facilitate cloning of the PCR fragment into the plant transformation vector (pBI121, CloneTech) as a translational fusion with the GUS gene.

The HindIII/BamHI fragment was cloned into the pBI121 expression cassette, replacing the 35S promoter and generating a translational fusion between the HPL upstream region and the GUS reporter gene. This construct was introduced into *Arabidopsis thaliana* (ecotype Columbia) by using the floral dip method (Clough S. J. and Bent A. F. Plant J. 16: 735–743). More than 250 Kanamycin resistant plants were made and grown to maturity. Leaf segments and flowers were removed from 150 plants to screen these plants for GUS reporter gene activity. Out of the total number of first generation plants assayed, 81 individual transformants showed strong GUS activity in leaf tissue and 67 showed strong GUS staining in the flower. Of these, 2 were chosen for further analysis.

Subsequent analysis of stable transformants indicated strong GUS staining throughout leaf tissue, both in young seedlings and mature plants. FIG. 2 demonstrates that in the root tips of young roots (FIG. 2A), the floral sepals (FIG. 2B) as well as the entire leaf (FIG. 2C) GUS staining is clearly evident. GUS staining was undetectable in the petals, style or pollen (FIG. 2B) and this was true even in transformants with very strong GUS expression To determine if the HPL regulatory region drives light-dependent expression, transformants were dark or light grown for 12 days and GUS histochemical analysis performed. Dark grown plants were observed and analyzed under a green safe light. Equivalent levels of GUS expression were found in plants grown under both conditions (data not presented) indicating that the promoter is not light-responsive.

To determine the inducibility of HPL-directed reporter gene expression, transformants were subjected to mechanical wounding by crushing leaf tissues with a serrated forceps and sliced with a razor as previously described (Bate et al., 1998). At various time post-injury leaves were removed from the plant and tested for GUS activity. In addition, leaves were removed and immediately frozen in liquid nitrogen. Subsequently, RNA was isolated from these tissues and used to perform Northern blot analysis for GUS gene expression (FIG. 3). With either treatment, only constitutive expression was observed, and there was no significant alteration in GUS expression observed in response to wounding.

Expression in Other Species

The activity of the HPL regulatory region, along with 35S for comparison, was also examined in a range of species using a transient assay outlined below. The constructs tested are presented in Table 1.

TABLE 1

Construct and vector information of regulatory regions

| Description | Construct | Vector |
| --- | --- | --- |
| HPL regulatory region | HPL-gus-nos | pBluescript II KS |
| 35S* | 35S-gus | pUC 19 |
| pBluescript II KS-ve control | empty vector | |

*35S-Gus from Clontech, Palo Alto

Plant tissue were obtained from a range of plants as indicated in Table 2.

TABLE 2

Taxonomic list of species analysed for HPL regulatory region activity

| GYMNOSPERMAE ANGIOSPERMAE | Pinaceae | White spruce |
| --- | --- | --- |
| DICOTS: | Cruciferae | Cauliflower |
| | Leguminoseae | Soybean, Alfalfa |
| | Rosaceae | Peach |
| | Solanaceae | Tobacco |
| | Vitaceae | Grape |

Soybean leaves were harvested from Harosoy 63 plants grown in a growth chamber. The youngest leaves were chosen from the 1$^{st}$ to 5$^{th}$ nodes from the tip of the shoot. The leaves were sterilised according to 30 seconds in 70% EtOH, 10 minutes in 2% v/v bleach and 3 repetitions of 3 minute rinses in sterile distilled water. Leaflets were cut to 2–2.5 cm by 3 cm size and preincubated overnight adaxial side down on MS medium (Murashige and Skoog 1962) containing NAA and BA.

Peach leaves were harvested from growth chamber grown trees of cultivar Bailey. The leaves were sterilised according to 30 seconds in 70% EtOH, 10 minutes in 2% v/v bleach and 3 repetitions of 3 minute rinses in sterile distilled water. The bottoms and tips of the leaves were trimmed and explants were preincubated overnight adaxial side down on modified MS medium (Murashige and Skoog 1962) containing 2,4-D and BAP.

Wheat callus production was induced by placing 14–20 day-old embryos of the variety SuMais 3, embryo side down on callus induction Murashige and Skoog (MS) medium (Murashige and Skoog, 1962, Physiol. Plant. 15:473–497.) with 2,4-D, (Weeks J. T., Anderson O. D. and Blechl A. E. 1993. Pl. Phys. 102:1077–1084; Weeks, J. T. 1995. *Stable transformation of wheat by microprojectile bombardment.* In: Gene transfer to plants. Eds. I Potrykus and G. Spangenberg. Springer. p. 157–161). When significant callus production was observed within 5 to 31 days these were crushed onto filter paper, 4 embryos per plate and transferred to fresh media in preparation for bombardment.

Tobacco leaves were harvested from in vitro cultures maintained on MS medium (Murashige and Skoog, 1962). Leaves selected for bombardment were of uniform size and colour which were then preincubated on MS medium containing NAA and BA overnight prior to bombardment.

Alfalfa callus of variety N.4.4.2 maintained on alfalfa callus induction media (B5h) modified from Gamborg et al. 1968 (Brown and Atanassov, 1985 Plant Cell Tiss. Org. Cult. 4: 111–122.).

Embryonal tissues of white spruce were intitiated following the method of Tremblay (1990, Can. J. Bot. 68:236–242), and were maintained by subculturing on half-strength LM medium (Litvay et al., 1985, Plant Cell Rep. 4:325–328; 1985) containing 10 μM 2,4-D (2,4-Dichlorophenoxyacetic acid) and 0.5 μM (6-Benzylaminopurine). Cultures were subcultured every 10 to 14 days and maintained in the dark at 25 C. For evaluation of HPL expression, 0.55 gram of tissues was weighed out under axenic conditions, spread evenly on sterile filter paper and placed on LM medium. Callus was then incubated on the medium overnight prior to bombardment.

Construct DNA was extracted and purified using the MAXI protocol of the Quiagen Plasmid Purification System. Each sample was diluted to a concentration of 1 μg/μl for use in the bombardment protocol.

Prior to bombardment tungsten particles were coated with transforming DNA by adding the following chilled sterile solutions in order 5 μL DNA, 25 μL 2.5 M CaCl$_2$ and 5 μL spermidine. Tissue was bombarded with 2 μL of the DNA/tungsten solution or in the case of co-bombardment with OxO (oxaltate oxidase; see below) constructs 2 μL of the mixed DNA/tungsten solution. The settings were 100 psi pressure for wheat and 150 psi pressure for tobacco, soybean, peach, alfalfa, cauliflower and grape with the tissue sitting at position 10 in the particle bombardment device (Brown et al. 1994 Plant Cell Tiss. Org. Cult. 4: 111–122; Buckley et al. 1995).

For histochemical analysis the tissue was covered with 3 L GUS incubation buffer and left overnight in the dark at 37° C. Visual counts were made of positive GUS staining using a dissecting microscope.

For fluorometric analysis tissue was collected and ground in liquid nitrogen and either stored at −80° C. or immediately extracted folowing protocols modified from Gartland et al. (1995, *Fluorometric GUS analysis for transformed plant material.* In: Methods in Molecular Biology, Vol. 44: *Agrobacterium Protocols*. Eds:K. M. A. Gartland and M. R. Davey Humana Press Inc., Totowa N.Y. Pp 195–199) and Vitha et al. (1993, Biologia Plantarum 35(1):151–155). Fluorometric readings were taken on a RF-Mini 150 Recording Fluorometer, and protein content was assessed using a Bradford assay read in the BioRad Model 2550 EIA Reader. Fluorometric data was analysed using Lotus 123 and Microsoft Excel.

Histochemical Data

The hydroperoxide lyase promoter isolated from *Arabidopsis* was transiently active in all species tested as shown in tables 3 and 4 following microprojectile bombardment. Transient expression was also observed in grape leaves following bombardment with results not shown.

TABLE 3

Histochemical determination of transient expression of the HPL regulatory region in dicot species.

| Regulatory Region | Number of blue foci ± standard error | | | | |
|---|---|---|---|---|---|
| | Soybean | Alfalfa | Tobacco | Cauliflower | Peach |
| HPL | 2479 ± 216 | 39 ± 12 | 484 ± 147 | 9 ± 4.5 | 183 ± 102 |
| 35S | 1069 ± 407 | 161 ± 31 | 518 ± 145 | 67 ± 22 | 268 ± 243 |
| pBluescript II KS (−ve control) | 31 ± 20 | 0 | 0 | 0 | 0 |

TABLE 4

Histochemical determination of transient expression of HPL regulatory region in gymnosperm species.

| Regulatory region | Number of blue foci ± standard error White Spruce |
|---|---|
| HPL | 69 ± 27 |
| 35S | 116 ± 6 |
| pBluescript II KS (−ve control) | 0 |

These results show that the HPL regulatory region is active within a variety of organisms, including angiosperms and dicots. Furthermore, the activity of the HPL regulatory region in these varied organisms is equivalent to that of 35S.

Fluorogenic Data

Fluorogenic analysis of transient expression of GUS using the HPL regulatory region in soybean is present in Table 5.

TABLE 5

Flurogenic analysis of HPL regulatory region in soybean (Harosoy 63)

| Promoter | Transient expression in soybean leaflets GUS pmol/hr/mg |
|---|---|
| HPL | 4549.5 ± 1832.9 |
| 35S | 2306.7 ± 77.5 |
| pBluescript II KS (−ve control) | 2079.9 ± 1988.3 |

Example 2

HPL-PAT Expression

A construct was generated whereby the PAT open reading frame (ORF) which encodes phosphinotricin-N-acetlytransferase conferring resistance to phosphinotricin (Liberty, Basta, Glufosinate Ammonium) was placed under the control of the HPL promoter. An ~850 bp EcoRI fragment containing the PAT ORF and NOS terminator was isolated from pcwEnN::ID and cloned into the EcoRI site of pBluescript KS+ (Stratagene) such that the 5' end of the PAT gene was downstream of the NotI site in pBluescript. This construct contains a single NcoI site upstream of the ATG of the PAT ORF. The ~1.5 kb NotI/BamHI klenow filled fragment of the HPL regulatory region in pGEM-T-Easy (Promega) was cloned in front of the PAT/NOS terminator construct digested with NotI/NcoI klenow filled. A HindIII/EcoRI fragment containing the HPL regulatory region driving the PAT ORF/NOS terminator was cloned into the pBI121 (Clontech)expression cassette replacing the 35S promoter, GUS reporter gene and NOS terminator. The construct was introduced into *A. thaliana* (ecotype Columbia) using the floral dip method (Clough S. J. and Bent A. F. Plant J. 16: 735–743). Seedlings were first selected on 50 mg/L kanamycin. Transformed plants were sprayed with 3 g/L phosphinotricin using a spray chamber with the following configuration: XR Teejet 8002Vs spray head, 30 PSI, 2.25 km/h, automatic cycle. Three passes of the herbicide were made. Plants were re-sprayed 7–10 days after initial spraying. Resistant plants were compared to wt *Arabidopsis* and a control *Arabidopsis* line containing the PAT ORF.

These results indicate that plants expressing PAT were resistant to repeated spraying treatments of phosphinotricin.

Example 3

HPL-OV7 Expression

Vector Construction

Figure 4A:
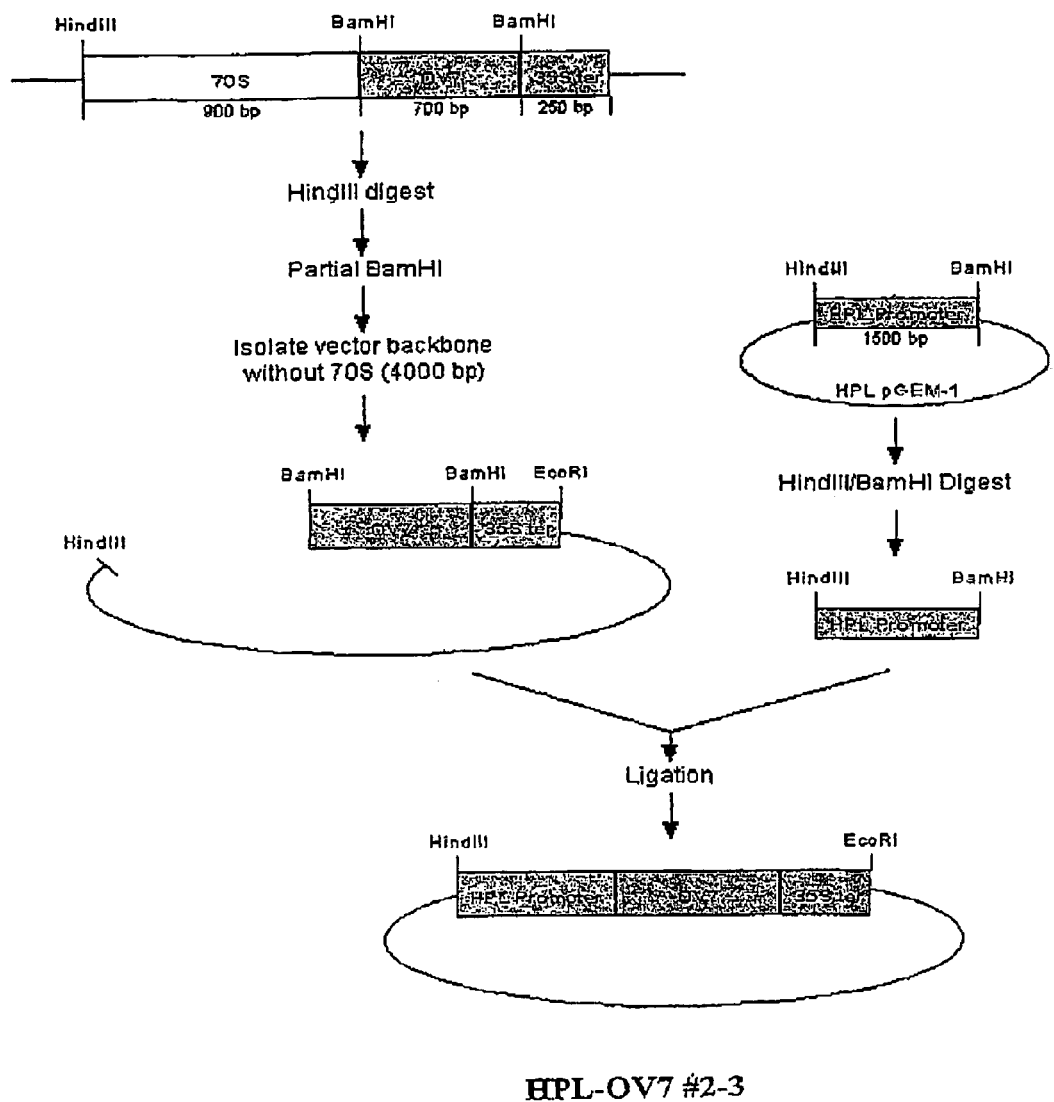
FIG. 4(A) shows HPLOV7 #2–3, and FIG. 4B) shows pCAMHPLOV7.

The HPL promoter in the pGEM T Easy vector was restricted with Hind III and BamHI to liberate a 1500 bp promoter fragment. The fragment was ligated into the partially digested—BamHI digest/Hind HIII digested sites of the 4000 bp vector plasmid containing the OV7 gene (onchocystatin) and the 35S poly A signal, thus generating HPL-OV7 #2–3 (FIG. 4(A)).

Figure 4B:
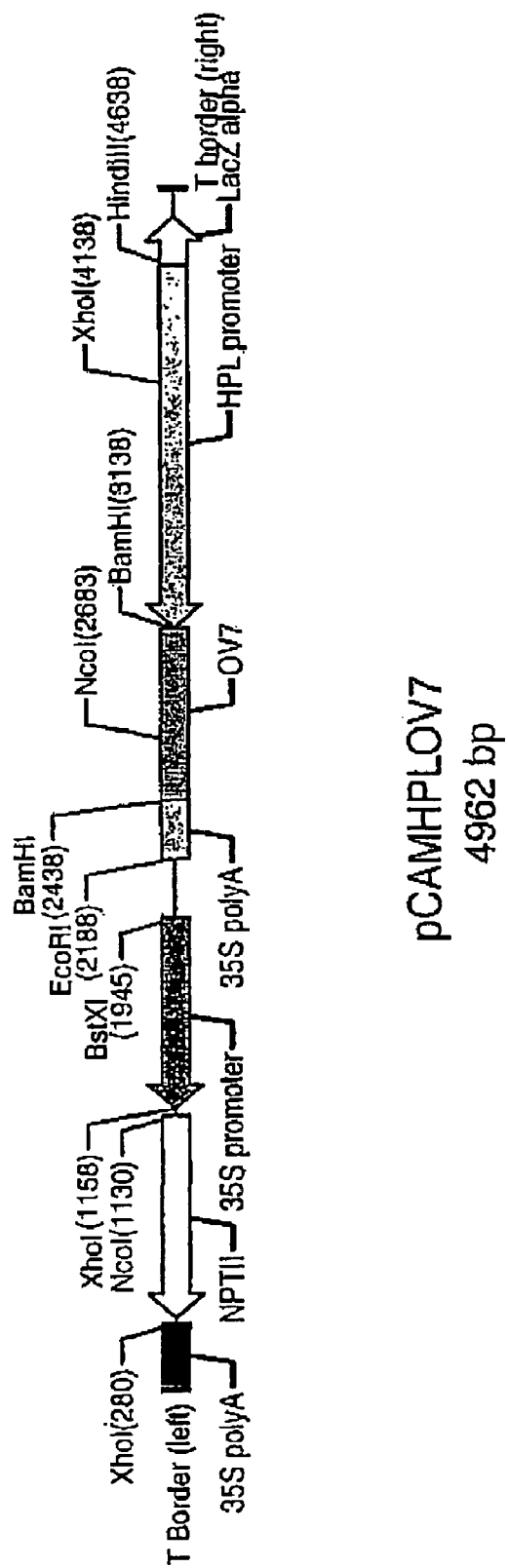
FIG. 4 shows the preparation of HPL vectors comprising onchosystatin (OV7 gene).

The 2450 bp HindIII/Eco RI digested fragment was removed from HPL-OV7. This contained the 1500 bp HPL promoter fragment, the OV7 coding sequence(700 bp), and the CAMV 35S polyA signal sequence (250 bp) and was then ligated into the binary *Agrobacterium* vector pCambia 2300 to produce the plasmid pCAMHPLOV7 (FIG. 4(B)). As a control, a tandem 35S-OV7 construct was also produced (70S-OV7 see FIG. 4(A)) and introduced into *B. Napus* as described below.

The pCAMHPLOV7 and 70S-OV7 constructs were then transformed into *Agrobacterium tumefasciences* strain GV3101. 100 ul of competent GV3101 cells were incubated with 5 ul of plasmid DNA on ice for 30 minutes, then quick frozen in liquid nitrogen. The tube was then thawed at 37° C. for minutes, and 1 mL of SOC medium was added to the tube. The cells were incubated 2 hrs at 28° C. with shaking at 200 rpm. The cells were spun down and resuspended in 150 uL liquid LB medium and plated on agar solidified plates of LB containing Rifampcin (50 ug/mL), Gentamycin (50 ug/mL), Kanamycin (50 ug/mlL for 2 days at 28° C.

Plant Transformation

Seeds of *B. napus* cv. Westar were surface sterilized by rinsing in 70% ethanol for 15 sec. followed by imersion in javex (1:3 dilution) for 20 min. Seeds were rinsed in sterile dH$_2$O and plated onto ½ strength homone-free MS medium (Murashige and Skoog 1962) containing 1% sucrose, solidified with 8 g/L phytagar, inside sterile Magenta boxes. Seeds were germinated in a growth room at 25° C. with a 16 hr. daylength supplied by incandescent and fluorescent lights (70–80 mE illumination) for 4–5 days.

*Agrobacteriumn* cultures (1 ml of overnight) were diluted into 40 mLs of liquid MS salts, 2% sucrose, 1 mg/L 2,4-D, and 10 ml/L DMSO. Forceps and sharp scalpels were used to dissect petioles from germinated canola seedlings, which were then placed into the liquid MS salts medium. The explants were incubated with the bacterial cells for 10 min at room temp and then the bacteria were removed by pipetting. The petri dishes containing explants were then sealed, covered in tin foil, and incubated at 28° C. in darkness for 2 days. The explants were then placed at 4° C. in darkness for 3–4 days of further co-culture. Explants were then placed on selection medium containing MS medium with 4 mg/L Benzylamino purine (BA), 3% sucrose, 0.7% phytagar, and 300 mg/L timentin, and 20 mg/L kanamycin. Explants were transferred to fresh selection plates after 1 week of selection and again after 3 weeks of selection. From this point shoots were selected which remained green, and all explants were subsequently transferred at 2 week intervals onto fresh selection medium.

Shoots were rooted on MS medium containing 3% sucrose, 4 mg/L NAA and 300 mg/L timentin, and 20 mg/L kanamycin. Once good root systems were established the transformants were transferred to Jiffy 7 peat pellets in the growth room for hardening for 1–2 weeks prior to transfer to the greenhouse. 139 independent transgenic lines were recovered and analyzed.

Northern Blotting

Total RNA was extracted from leaves of greenhouse plants using the TRIzol reagent method. Samples were harvested in liquid nitrogen, ground, and immersed into 1 mL of TRIzol reagent in a sterile tube. Samples were incubated at room temp for 5 min. and then placed on ice for 10 min, prior to centrifugation at 4° C. and 12,000 rpm for 10 min. Supernatants were transferred to fresh tubes and extracted with 200 µL chloroform. After centrifugation for 15 min at 4° C. the upper aqueous phase was transferred to fresh tubes and the RNA was precipitated with isopropanol and NaCl at −20° C. The pellets were washed with 80% ethanol in DEPC-treated water. The RNA pellets were re-suspended in 50 uL of DEPC-treated water.

Fifteen micrograms of total RNA was loaded into the wells of a formaldehyde MOPS gel and electrophoresed for 4–5 hours at 70 volts. Following UV documentation, the gel was transferred to nylon membranes by capillary transfer. Radiolabelled (32 P) DNA fragments of the OV7 gene were probed to the membranes overnight at 42° C., and washed in 0.2×SSC/0.1% SDS at 65° C. for 30 minutes. Autoradiograms were exposed for 5–7 days before developing.

Results from the Northern analysis of 20 plants transformed with either the 70S-OV7 or HPL-OV7 constructs are shown in FIG. 5. Lane 1-RNA ladder, Lane 2-tobacco plant expressing 70S promoter-OV7 gene, Lane 3-B. carinata plant expressing 70S promoter-OV7 gene, Lane 4-*B.napus* Westar non-transformed plant, Lane5-blank lane, no RNA sample, Lane 6-HPL-OV7 plant 11A, Lane 7-HPL-OV7 plant 15A, Lane 8-HPL-OV7 plant 18A, Lane 9-HPL-OV7 plant 27A, Lane 10-HPL-OV7 plant 28A, Lane 11-HPL-OV7 plant 32A, Lane 12-HPL-OV7 plant 33A, Lane 13-HPL-OV7 plant 36A, Lane 14-HPL-OV7 plant 39A, Lane 15-HPL-OV7 plant 49A, Lane 16-HPL-OV7 plant 51A, Lane 17-HPL-OV7 plant 65A, Lane 18-HPL-OV7 plant 80A, Lane 19-HPL-OV7 plant 81A, Lane 20-HPL-OV7 plant 82A.

These results show that OV7 expression under the control of the HPL regulatory region was detected plants at similar levels to that of the 70S promoter, and demonstrate that the HPL regulatory region is active in a range of plants and plant tissues.

All citations are herein incorporated by reference.

The present invention has been described with regard to preferred embodiments. However, it will be obvious to persons skilled in the art that a number of variations and modifications can be made without departing from the scope of the invention as described herein.

The invention claimed is:

1. A chimeric construct comprising a sequence obtained from a Hydroperoxide Lyase (HPL) gene selected from the group consisting of:
   a) a promoter sequence comprising SEQ ID NO:1;
   b) a promoter sequence comprising a fragment of SEQ ID NO:1 having promoter activity
   c) the full length complement of SEQ ID NO:1, and
   (d) the full length complement of the fragment identified in (b), wherein the promoter sequence is in operative association with a heterologous polynucleotide sequence of interest, and wherein the promoter sequence comprises HPL promoter activity and constitutively expresses the heterologous polynucleotide sequence of interest.

2. The chimeric construct of claim 1, wherein said promoter sequence is defined by the nucleic acid sequence of SEQ ID NO:1.

3. A transgenic plant comprising the chimeric construct of claim 1.

4. A transgenic seed comprising the chimeric construct of claim 1.

5. A transgenic cell culture comprising the chimeric construct of claim 1.

6. The transgenic cell culture of claim 5, wherein the cell culture is a plant cell culture.

7. A chimeric construct of claim 1, wherein said promoter sequence is in operative association with an enhancer sequence, so that both said promoter sequence and said enhancer sequence operate together to drive the expression of the polynucleotide sequence of interest.

8. A method of driving the expression of a polynucleotide sequence of interest in a non-human organism comprising;
   i) transforming said organism with the chimeric construct of claim 1 to produce a transformed organism; and
   ii) growing said transformed organism.

9. The method of claim 8, further comprising
   iii) determining the expression of said polynucleotide sequence of interest within said transformed organism.

10. The method of claim 8, further comprising
    iv). obtaining progeny expressing said polynucleotide of interest.

11. The method of claim 8, where said organism is a plant.

12. A method of driving the expression of a polynucleotide sequence of interest in a non-human organism comprising;
    i) transforming said organism with the chimeric construct of claim 7 to produce a transformed organism; and
    ii) growing said transformed organism.

13. The method of claim 12, further comprising
    iii) determining the expression of said polynucleotide sequence of interest within said transformed organism.

14. The method of claim 12, further comprising
    iii) obtaining progeny expressing said polynucleotide of interest.

15. The method of claim 12, where said organism is a plant.

16. An isolated nucleic acid comprising a sequence obtained from a Hydroperoxide Lyase (HPL) gene selected from the group consisting of:
    a) a promoter sequence comprising SEQ ID NO:1;
    b) a promoter sequence comprising a fragment of SEQ ID NO:1 having promoter activity
    c) the full length complement of SEQ ID NO:1 and
    d) the full length complement of the fragment identified in (b), wherein the promoter sequence comprises HPL promoter activity and is a constitutive promoter element.

* * * * *

UNITED STATES PATENT AND TRADEMARK OFFICE
CERTIFICATE OF CORRECTION

| | | |
|---|---|---|
| PATENT NO. | : 7,223,855 B2 | Page 1 of 1 |
| APPLICATION NO. | : 10/204234 | |
| DATED | : May 29, 2007 | |
| INVENTOR(S) | : Ulrike Schafer et al. | |

It is certified that error appears in the above-identified patent and that said Letters Patent is hereby corrected as shown below:

On The Title Page, Item (54)
In the title:

Please correct the spelling of "REGULATOR" to --REGULATORY--, making the title read --HYDROPEROXIDE LYASE REGULATORY REGION.--

Signed and Sealed this

Seventh Day of August, 2007

JON W. DUDAS
*Director of the United States Patent and Trademark Office*

SEQUENCE LISTING

<160> NUMBER OF SEQ ID NOS: 3

<210> SEQ ID NO 1
<211> LENGTH: 1480
<212> TYPE: DNA
<213> ORGANISM: Arabidopsis thaliana

<400> SEQUENCE: 1

```
aacgtggata cttggcagtg gttacttggc ttttccttta ttttcttttg gacggaagcg      60
gtggttactt tgtcacacat ttaaaaaaac acgtgtttct cactcttttc tattcccgtc     120
acaaacaatt ttaagaaaga tcgatctatc gtgatctttc tatcaaacaa aagaaaaaag     180
gtcttcatag taacgctaca acatcaaata tgtggttgct ctgacatcag tcgggaaaat     240
aaggatatgg cgccattggc cacatctatt ggggtcccaa cttcctttca caaaaaaatt     300
aaattgggtg acccaacttt tatctttgat atagtgacat gagtatcggg agcattggac     360
aatggataaa atgagaacta aacaaattct ggttaatttt tgatcattgt tatttaaaag     420
gttattttat ctataatcta cccatattga tcagttttat ttaaatttgt ttagctaccg     480
ctcctcgaga gagatcctca tcttaaaaat ggaatatgga aattacacac gaccccaaaa     540
gtatattttt tctctggaga atgctattta gagctttgac tatatggtct gaattagaaa     600
gacgggaaat aaaatctgct aagtgatata agctctaagt aggcgatgtg tgatggagaa     660
caccttttct ttaacagtct tcatgtttta cagattcgcg aacttcgaat atccctatac     720
ggtctgtcta accctcgtgt gtcttttgag tccaagataa aggccattat tgagtaacat     780
agacatgctg gaatccaacc attgaagtca caactgtcca tgtagattct ttggagaatc     840
tgaaaagtct taataaaggt ggtgtttcaa agaaaacaaa acaattgagt taagaaaaaa     900
aaatatcatg tagtggtcga gtattatgtt atttattgtg tagctaccaa tctttattct     960
ttaaatctga cataaaatgc tacaaacttt ttacctcgtc tatagcccca aaaaacctaa    1020
ccacggttct aaaaccacac acagtgattt tggttgacga caatgcctct ccttcctcaa    1080
aacgatttat ttacatttt taaatcaaat gttacatttt ataccataat taagtctttt    1140
tacagaatac ttgatggaa gagatgtata aaaaggagg aaattgtaaa aaacatattt    1200
cgatcaatta aaccaggatt cataaaaata taagtatata tataaatgat gtttcgttta    1260
gcgatgaact tcactcatat gataatactt aacaatataa gtacataaaa aataaaataa    1320
```

```
aattaattgt ttacgaaaag tctacaaata ctgcatgtat aattaatgtt ctctttattt      1380
atttatttat accttaccaa gatatatcta taaccgcata gaaatagaag gcgaagagat      1440
aatttccaaa aacaagaaaa acctctaagc tcaaaagatg                            1480

<210> SEQ ID NO 2
<211> LENGTH: 20
<212> TYPE: DNA
<213> ORGANISM: artificial sequence
<220> FEATURE:
<223> OTHER INFORMATION: synthetic

<400> SEQUENCE: 2
ggaagcttgc cataacgtgg                                                  20

<210> SEQ ID NO 3
<211> LENGTH: 21
<212> TYPE: DNA
<213> ORGANISM: artificial sequence
<220> FEATURE:
<223> OTHER INFORMATION: synthetic

<400> SEQUENCE: 3
tcggatccca tcttttgagc t                                                21
```